US011521729B1

(12) United States Patent
Al-Fahl

(10) Patent No.: US 11,521,729 B1
(45) Date of Patent: *Dec. 6, 2022

(54) SECURE MEDICATION DISPENSER

(71) Applicant: Mohammed-Tarek Al-Fahl, Houston, TX (US)

(72) Inventor: Mohammed-Tarek Al-Fahl, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/821,571

(22) Filed: Mar. 17, 2020

Related U.S. Application Data

(63) Continuation of application No. 15/155,512, filed on May 16, 2016, now Pat. No. 10,592,638.

(60) Provisional application No. 62/161,941, filed on May 15, 2015, provisional application No. 62/335,798, filed on May 13, 2016.

(51) Int. Cl.
*G16H 20/13* (2018.01)
*G05B 19/042* (2006.01)

(52) U.S. Cl.
CPC .......... *G16H 20/13* (2018.01); *G05B 19/042* (2013.01); *G05B 2219/24159* (2013.01)

(58) Field of Classification Search
CPC .............. G06F 19/3462; G05B 19/042; G05B 2219/24159; G16H 20/13
USPC ................................. 700/231–244
See application file for complete search history.

(56) References Cited

U.S. PATENT DOCUMENTS

| | | | | |
|---|---|---|---|---|
| 5,009,330 A | * | 4/1991 | Young | G07F 11/44 221/265 |
| 6,203,249 B1 | * | 3/2001 | Ishida | H01L 21/67721 221/233 |
| 7,044,302 B2 | * | 5/2006 | Conley | A61J 7/0472 206/538 |
| 7,743,923 B2 | * | 6/2010 | Conley | A61J 7/0481 206/534.1 |
| 10,592,638 B1 | * | 3/2020 | Al-Fahl | G05B 19/042 |
| 2008/0203107 A1 | * | 8/2008 | Conley | G07F 11/16 221/1 |
| 2010/0305750 A1 | * | 12/2010 | Conley | A61J 7/0427 700/237 |
| 2014/0148947 A1 | * | 5/2014 | Levesque | G07F 17/0092 700/237 |

* cited by examiner

*Primary Examiner* — Michael Collins
(74) *Attorney, Agent, or Firm* — Wayne Edward Ramage; Baker Donelson

(57) ABSTRACT

A secure medication dispenser or apparatus dispensing only prescribed amounts of controlled medication (e.g., pain medication, narcotics and the like) on a limited, periodic basis. Medication is dispensed through an access slot. The dispenser cannot be opened by the user or any third party except on this limited, periodic basis. The dispenser is manufactured from strong, penetration-resistant material, and cannot easily be broken, smashed, cut, or otherwise opened.

20 Claims, 9 Drawing Sheets

SECURE MEDICATION DISPENSER

This application is a continuation of U.S. application Ser. No. 15/155,512, filed May 16, 2016, which claims benefit of and priority to U.S. Provisional Application No. 62/335,798, filed May 13, 2016, and No. 62/161,941, filed May 15, 2015, and is entitled to those filing dates for priority. The specifications, figures, and complete disclosures of U.S. Provisional Application Nos. 62/335,798 and 62/161,941 and U.S. application Ser. No. 15/155,512 are incorporated herein in their entireties by specific reference for all purposes.

FIELD OF INVENTION

This invention relates to a secure medication dispenser or apparatus.

BACKGROUND OF THE INVENTION

A variety of medicine containers and dispensers that provided limited or timed access to medication are known in the art. Examples include Abdulhay, et al., U.S. Pat. No. 7,711,449 (disclosing automated pill dispenser with multiple chambers and feed mechanisms programmably operable by the user or by remote input from PDA or similar device); Ratnakar, U.S. Pat. No. 8,483,872 (disclosing a dispenser with internal conveyors and counters subject to control by external computer servers), Ervin, U.S. Pat. No. 8,666,539 (disclosing a pill container with access code obtained from external master computer system), and Dunn, US 2013/0166066 (disclosing electronic dispenser with location determination device connected to web applications server), all of which are incorporated herein by specific reference in their entireties for all purposes.

However, there remain significant problems with the prior art. Several of the devices are large and bulky, not easily transportable, and contain complicated delivery mechanisms that often fail or break. And many devices are not truly secure, and do not prevent untimely access to the medication supply. Accordingly, what is needed is an improved medication dispenser that addresses these problems.

SUMMARY OF INVENTION

In various exemplary embodiments, the present invention comprises a secure medication dispenser, dispensing only prescribed amounts of controlled medication (e.g., pain medication, narcotics and the like) on a limited, periodic basis. Medication is dispensed through an access slot. The access slot may be open, or it may be covered or closable (such as with a sliding door or cover) and lockable. The dispenser cannot be opened by the user or any third party except on this limited, periodic basis. The dispenser is manufactured from strong, penetration-resistant material (such as steel, metal, hardened plastic, or the like), and cannot easily be broken, smashed, cut, or otherwise opened.

The dispenser comprises a compact main body (such as in the shape of a disk or oval with thickness, although other shapes are possible), with a rotating series of chambers therein. Some or all chambers contain a prescribed dose of the medication. Some chambers may be left empty, or comprise a solid wall or block (e.g., as a home position). A timer or display screen may be located on the top, bottom or sides, along with a keypad, which can be electronic or mechanical. The display also may be a touch display screen, and the keypad or authorization input means can be presented and used thereon. The timer shows the time, or the time remaining until the access period starts. The display screen and keypad also may be located on the sides or bottom of the device.

In several embodiments, the keypad comprises rubberized or covered soft buttons, and are flush or recessed from the surface to prevent a button from accidentally being pushed. A full set of numbered or alpha-numeric keys may be provided, or a simple 3 or 4 button arrangement (e.g., one up button and one down button to select numbers or alpha-numeric characters in sequence, and an enter button for selection).

During the access period, the device indicates in some fashion through an alarm or an alert (flashing display, instructions on display, audible alarm from a speaker, beeper, or combinations thereof) that the user should input a PIN or access code to the device through the keypad or input means. The duration of the alarm or alert can last the entirety of the access period, or only some portion thereof. If the PIN or access code is correctly entered during the access period, the internal mechanism rotates the chamber with medication for that access period (which may be the next chamber in sequence, or a designated chamber) to a portion of the main body where medication can be removed. In one embodiment, the medication leaves the chamber through an opening and passes through a passageway inside the main body to the access slot. In an alternative embodiment, the chamber is aligned with the access slot, which is open or opens, allowing the user to obtain the prescribed amount of medication for that particular dose. Access requires the PIN or access code be entered within the proper access time period. Entering the PIN or access code outside the proper access period will not allow access to the medication.

The access slot may be located at various points on the perimeter of the main body of the device. It also may be located on the top, sides, or bottom of the device. The access slot may directly align with the appropriate chamber, or an opening in the chamber. Alternatively, chambers are rotated to align with one end of an internal passage. As the chamber is rotated to align with the end of the internal passage, the end of the internal passage is opened, allowing passage of the medication from the chamber through the internal passage to the access slot. Alternatively, this end of the internal passage may remain open at all times. A rim or edge may be provided to prevent medication from simply exiting the chamber without moving or shaking the device, or turning it or rotating it vertically so that the medication falls out of the chamber. In one particular embodiment, the opening of the inside end of the internal passage may be offset along one or more sides (e.g., the bottom of the internal passage is higher than the bottom of the chamber).

If the user wishes to bypass taking the medication for a particular access period, the user may enter a bypass code, whereupon the device will cease the alarm or alert until the next access period. The timing and length of access periods can vary. The dosing interval can be set at a constant period (e.g., 4 hours, 6 hours, and so on), or may vary.

The amount of time the user has to remove the medications may be the remaining length of the access period, or a shorter time period. The movement of the internal rotary mechanism may be delayed for a period of time after entry of the access code. The internal rotary mechanism will move or the access slot will close after expiration of the time period, regardless of whether medication has been removed, in order to prevent subsequent access to the medicine.

In several embodiments, the internal mechanism comprises a rotary wheel, carousel or component with a plurality of chambers. The rotary wheel or component is rotated in a step-wise fashion by a motor powered by a power source, such as a fixed internal battery or batteries. In alternative embodiments, one or more replaceable or removable batteries or a power cord connected to an electrical outlet, or the like. The battery (or batteries) may be rechargeable. If batteries are replaceable, the battery access door is locked to prevent tampering by the user. The motor and other components of the device are governed by a controller, which determines when the motor moves the rotary wheel or component, and other device operations as described herein.

DETAILED DESCRIPTION OF EXEMPLARY EMBODIMENTS

In various exemplary embodiments, as seen in FIGS. 1-9, the present invention comprises a secure medication dispenser 2, dispensing only prescribed amounts of controlled medication (e.g., pain medication, narcotics and the like) on a limited, periodic basis. Medication is dispensed through an access slot 10. The access slot may be open, or it may be covered or closable (such as with a sliding door or cover) and lockable. The dispenser cannot be opened by the user or any third party except on this limited, periodic basis. The dispenser is manufactured from strong, penetration-resistant material (such as steel, metal, hardened plastic, or the like), and cannot easily be broken, smashed, cut, or otherwise opened.

Figure 1:
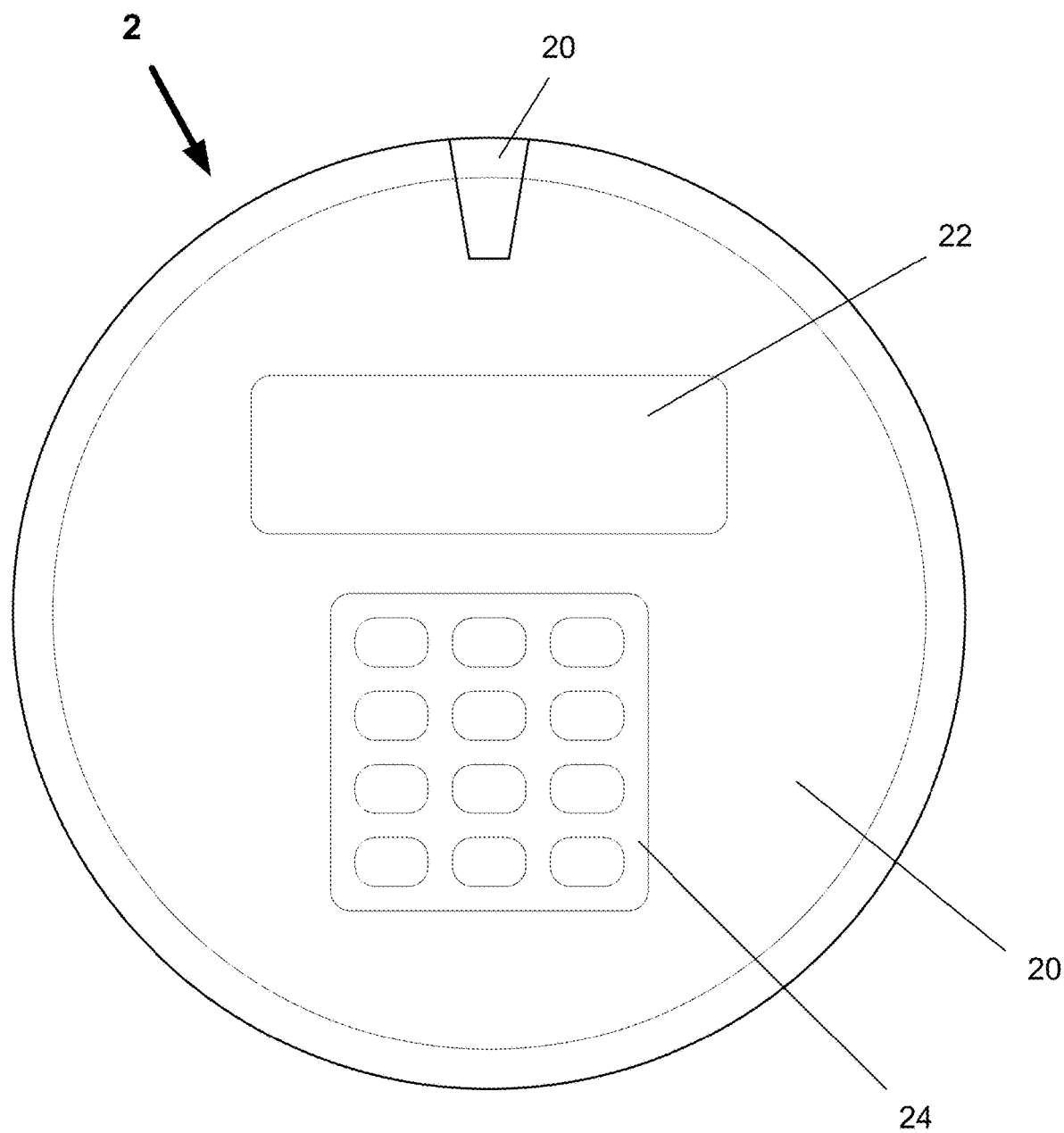
FIG. 1 shows a top view of a device in accordance with an embodiment of the present invention.
Figure 2:
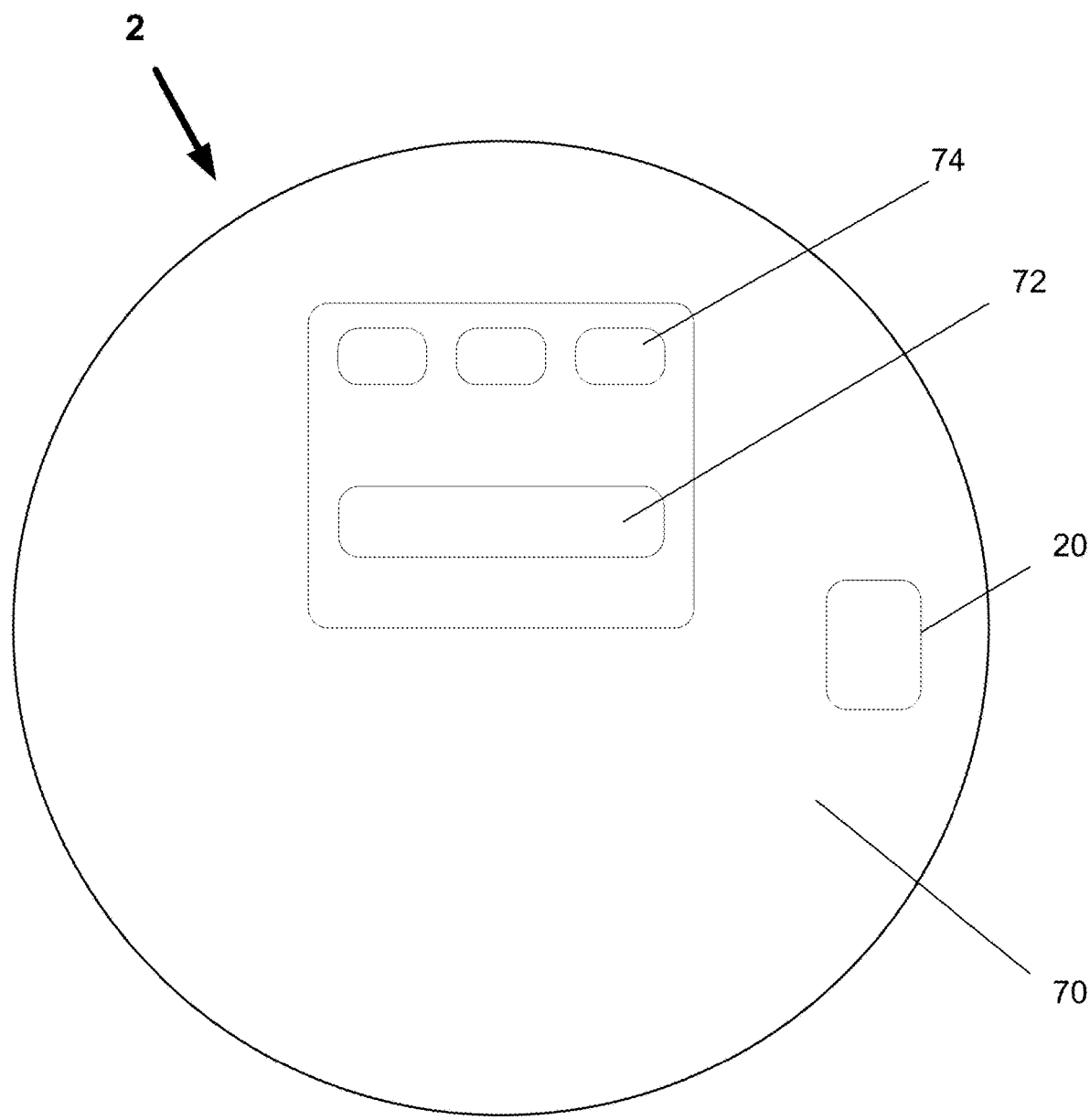
FIG. 2 shows a bottom view of another embodiment of the present invention.
Figure 3:
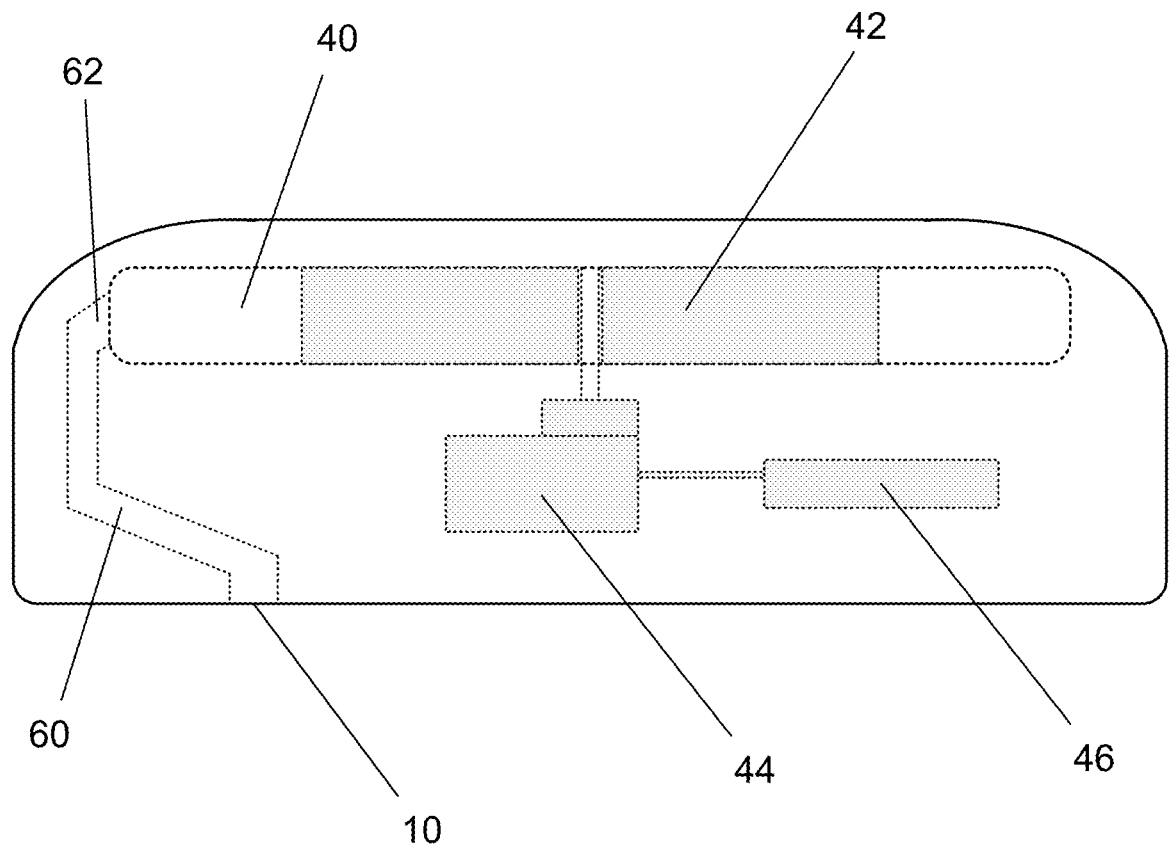
FIG. 3 shows a cutaway side view of the device of FIG. 2.
Figure 4:
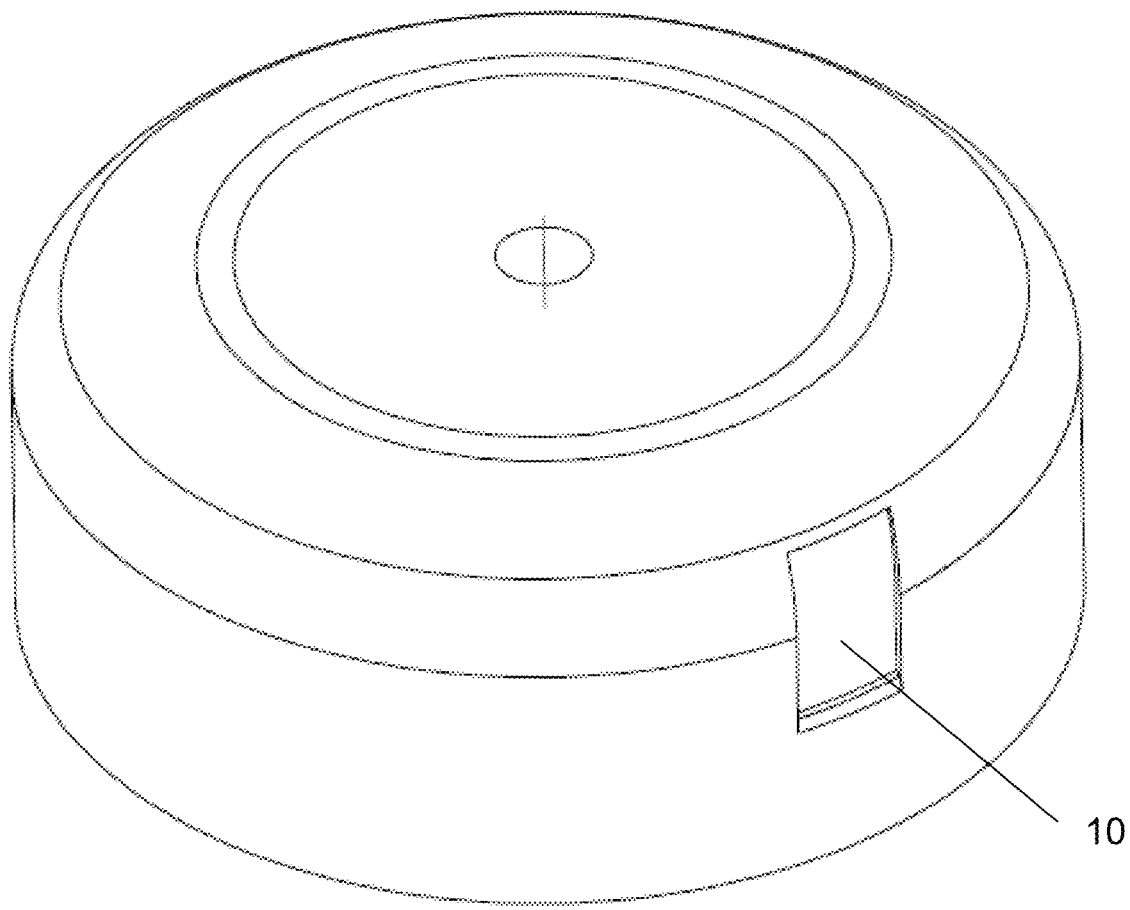
FIG. 4 shows a perspective view of another embodiment of the present invention.
Figure 5:
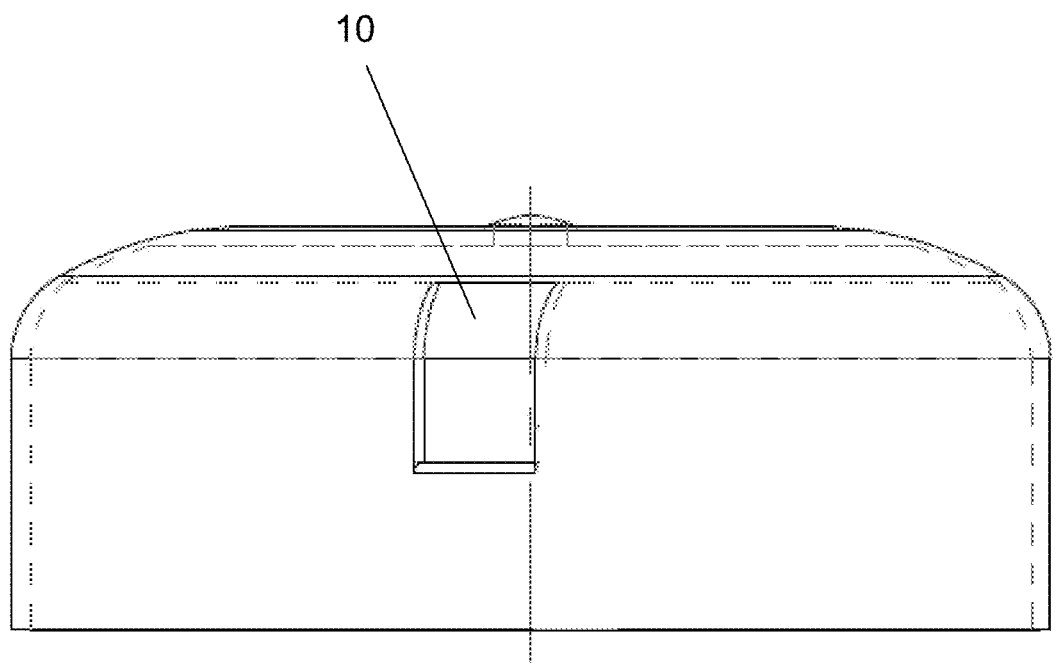
FIG. 5 shows a side view of the device of FIG. 1.
Figure 6:
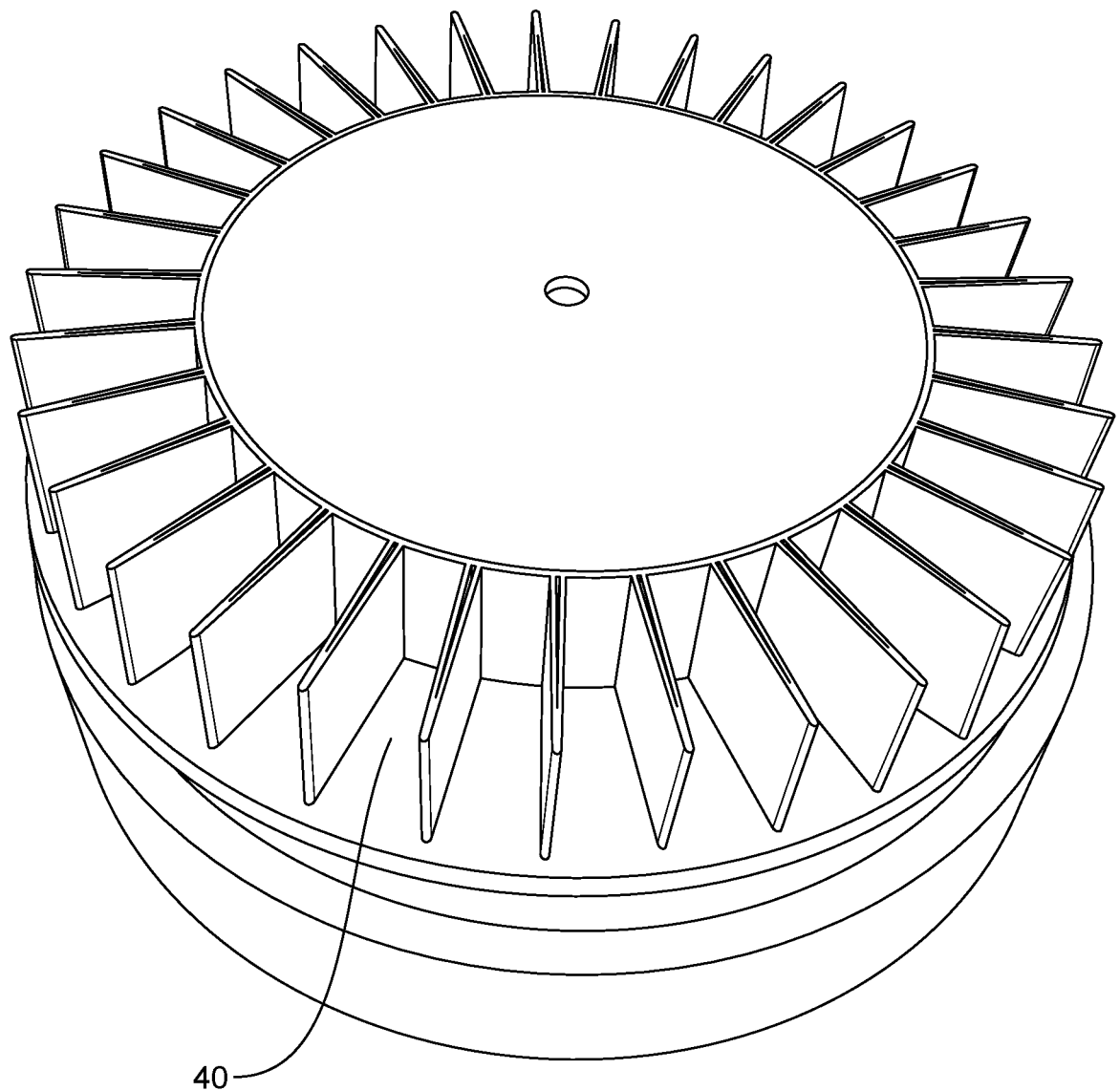
FIG. 6 shows a view of a rotary wheel or carousel.
Figure 7:
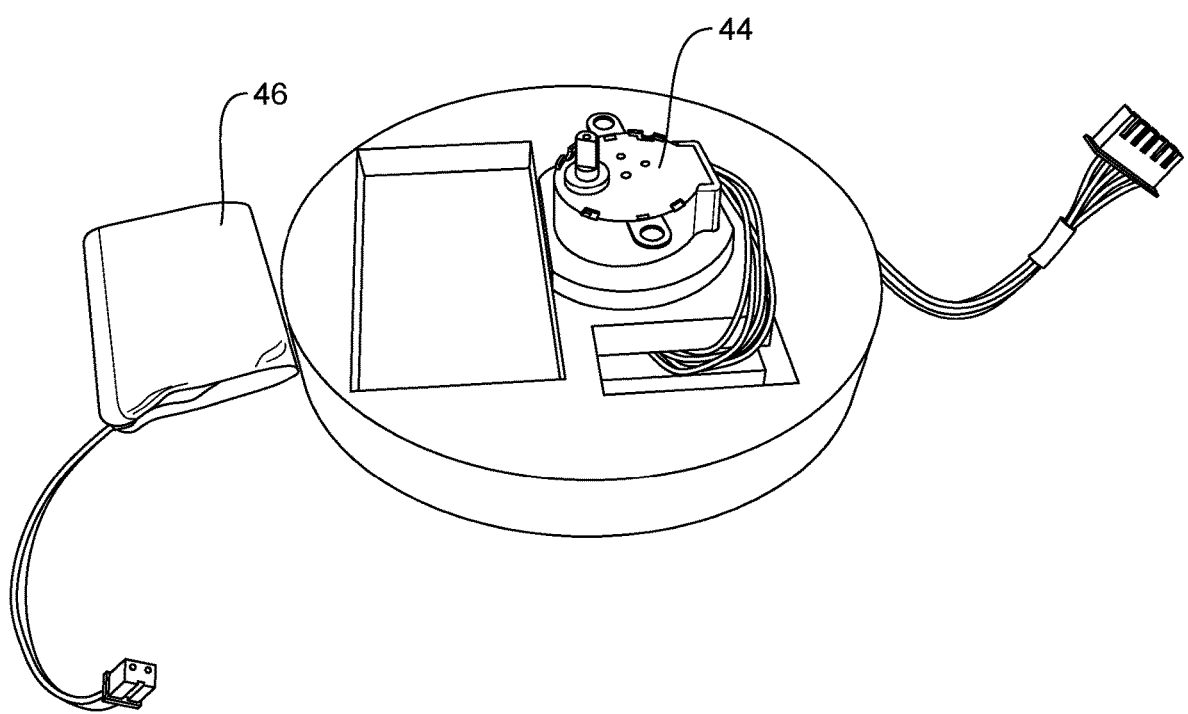
FIG. 7 shows a view of an exposed base of the device, with a motor and battery.
Figure 8:
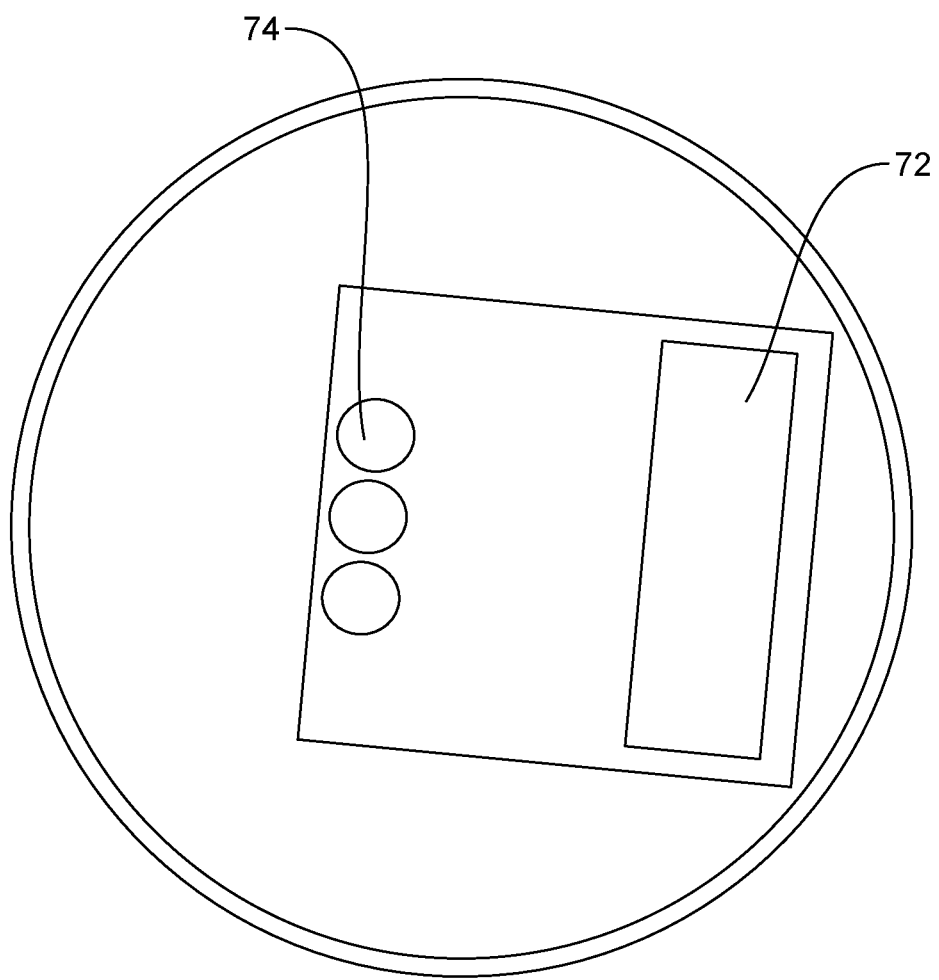
FIG. 8 shows a bottom view of another embodiment of the present invention.
Figure 9:
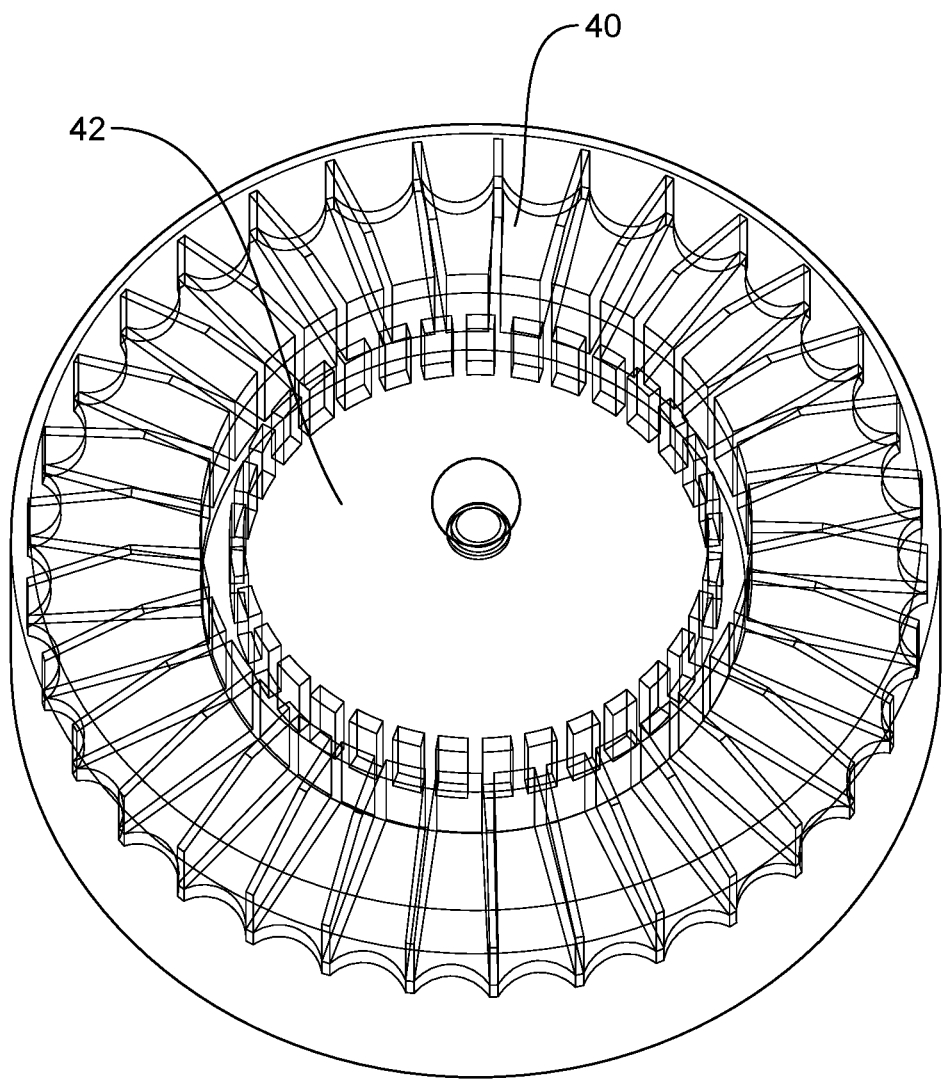
FIG. 9 shows a perspective view of a rotary wheel or carousel.

The dispenser comprises a compact main body 20 (such as in the shape of a disk or oval with thickness, as seen in FIGS. 1 and 2, although other shapes are possible), with a rotating series of chambers 40 therein. Some or all chambers 40 contain a prescribed dose of the medication. Some chambers may be left empty, or comprise a solid wall or block (e.g., as a home position). A timer or display screen 22 may be located on the top, bottom or sides, along with a keypad 24, which can be electronic or mechanical. The display also may be a touch display screen, and the keypad or authorization input means can be presented and used thereon. The timer shows the time, or the time remaining until the access period starts. The display screen and keypad also may be located on the sides or bottom of the device.

In several embodiments, the keypad comprises rubberized or covered soft buttons, and are flush or recessed from the surface to prevent a button from accidentally being pushed. A full set of numbered or alpha-numeric keys may be provided, or a simple 3 or 4 button arrangement (e.g., one up button and one down button to select numbers or alphanumeric characters in sequence, and an enter button for selection), as seen in FIG. 2.

During the access period, the device indicates in some fashion through an alarm or an alert (flashing display, instructions on display, audible alarm from a speaker, beeper, or combinations thereof) that the user should input a PIN or access code to the device through the keypad or input means. The duration of the alarm or alert can last the entirety of the access period, or only some portion thereof. If the PIN or access code is correctly entered during the access period, the internal mechanism rotates the chamber with medication for that access period (which may be the next chamber in sequence, or a designated chamber) to a portion of the main body where medication can be removed. In one embodiment, the medication leaves the chamber through an opening and passes through a passageway inside the main body to the access slot 10. In an alternative embodiment, the chamber is aligned with the access slot 10, which is open or opens, allowing the user to obtain the prescribed amount of medication for that particular dose. Access requires the PIN or access code be entered within the proper access time period. Entering the PIN or access code outside the proper access period will not allow access to the medication.

The access slot may directly align with the appropriate chamber, or an opening in the chamber. Alternatively, chambers 40 are rotated to an access position to align with one end 62 of an internal passage 60. As the chamber is rotated to align with the end of the internal passage, the end of the internal passage is opened, allowing passage of the medication from the chamber 40 through the internal passage 60 to the access slot 10. Alternatively, this end of the internal passage may remain open at all times. A rim or edge may be provided to prevent medication from simply exiting the chamber without moving or shaking the device, or turning it or rotating it vertically so that the medication falls out of the chamber. In one particular embodiment, the opening of the inside end of the internal passage may be offset along one or more sides (e.g., the bottom of the internal passage is higher than the bottom of the chamber).

The access slot may be located at various points on the perimeter of the main body of the device, as seen in FIG. 1. It also may be located on the top, sides, or bottom of the device, as seen in FIG. 2. While the access slot may be located in any position, in several exemplary embodiments, with the device held in a vertical position with the display screen or keypad in an up or upright orientation (e.g., for entry of the access code), the access slot may be located along the upper half of the perimeter (e.g., at 9, 10, 11, 12, 1, 2 or 3 o'clock positions), or in the upper half of the device. This prevents the medication from prematurely falling out of the dispenser while the access code is being entered. Alternatively, wherein an internal passage is present, the access position may located in the upper half of the device, while the access slot may be located elsewhere, including the bottom half of the device.

If the user wishes to bypass taking the medication for a particular access period, the user may enter a bypass code, whereupon the device will cease the alarm or alert until the next access period.

The timing and length of access periods can vary. For example, the length of an access period can be 15 minutes, 30 minutes, an hour, or some other time period. The length of sequential access periods can be the same, or may vary. Similarly, each access period can be set to start at particular times (e.g., 2 pm, 4 pm, 8 pm, and so on), or may be started at a measured interval from an action or lack of action during the previous access period. For example, if 4 hours is the dosing interval, then the subsequent access period can start 4 hours after the correct entry of the PIN or access code during the earlier access period (if the user has accessed the medication), or 4 hours after the entry of the bypass code to stop the alarm or alert (if the user has entered the bypass code), or 4 hours after the start (or end) of the earlier access period (if the user has not taken any action at all). The interval can be set at a constant period (e.g., 4 hours, 6 hours, and so on), or may vary.

The amount of time the user has to remove the medications may be the remaining length of the access period, or a shorter time period. The movement of the internal rotary mechanism may be delayed for a period of time after entry of the access code. For example, the delay may be 10 or 20 seconds after entry of the code, followed by rotation of the rotary mechanism to the correct chamber for access and opening of the access slot for 30 seconds or 60 seconds (or other established time period). The internal rotary mechanism will move or the access slot will close after expiration of the time period, regardless of whether medication has been removed, in order to prevent subsequent access to the medicine.

In several embodiments, the internal mechanism comprises a rotary wheel, carousel or component 42 with a plurality of chambers 40. The rotary wheel or component is rotated in a step-wise fashion by a motor 44 powered by a power source, such as a fixed internal battery or batteries 46 (a plastic tab can be installed during manufacturing to prevent completion of the power circuit; the tab is removed when the device is prepared for use, thereby completing the circuit and providing power to the device). In alternative embodiments, one or more replaceable or removable batteries or a power cord connected to an electrical outlet, or the like. The battery (or batteries) may be rechargeable. If batteries are replaceable, the battery access door is locked to prevent tampering by the user. The motor and other components of the device are governed by a controller, which determines when the motor moves the rotary wheel or component, and other device operations as described herein.

Upon entry of the PIN or access code during the access period, the interior rotary mechanism of the device rotates sufficiently to move a chamber with medication adjacent to the interior end of the interior passage or adjacent to the access hole. The interior passage may be straight, angled, or curved, in whole or in part. In one exemplary embodiment, the passage comprises at least one bend. In one embodiment, the passage comprises at least one bend of approximately 45 to 90 degrees.

As described above, the hole may remain open, or be closable between access times. In one embodiment, the hole closes and locks after it is opened, and remains locked until a correct PIN is entered during a subsequent access period.

In one embodiment, if access is not authorized, the internal mechanism does not rotate, and cannot be rotated until the next potential access period. Depending on the programming of the controller, upon entry of the PIN or access code during the next access period, the internal rotary mechanism may advance to the next chamber in the sequence (i.e., no chamber is bypassed), or may bypass the chamber (or chambers, if multiple access periods were skipped) that would have been accessed, thereby preventing access to the medication in those chambers. Since rotation of the interior mechanism only occurs with entry of the PIN or access code during an access period, access to the other chambers is prevented. The bypass embodiment limits access to a particular dose of medication to a particular access period in sequence.

Alternatively, the internal mechanism may rotate to the next chamber with each new potential access period (or continually rotates), with the slot opening only upon entry of the PIN or access code. The access hole may be open, or be closable and lockable, as described above. If access is not authorized, continued rotation causes that chamber and medication contained there to be bypassed. In this embodiment, each particular chamber is tied to a particular access period. This may be particularly useful when different medications are taken at different times during the day.

In one embodiment, the internal rotary mechanism rotates only in one direction during normal operation of the device. A physical stop or ratcheting mechanism may be provided to prevent the rotary wheel or carousel from being rotated in the other direction.

In another embodiment, the internal rotary mechanism can rotate in either direction. The rotary mechanism may default to a home position between access periods, and will only rotate to a particular chamber upon entry of a PIN or access code, as described above.

In several embodiments, the access slot is protected by a fixed cover, which may be integrated with the main body. The cover is open at the bottom, allowing the accessed medication to drop from the access slot to a receptacle along the side or bottom of the device.

The device may comprise several components. The main body may be integral, or may comprise a cover or shell that fits securely over and is fastened to the device base. The device base includes a bottom with several openings therein to hold recessed displays or key pads, a secured door for batteries, and the like. As seen in FIG. 2, the bottom comprises a display screen 72 with three recessed control buttons 74. A insert may be affixed to the inside of the bottom to provide spaces or means to securely hold a motor, power source, batteries, controller, or the like. A rotary wheel or carousel is mounted above the motor insert, and is connected to the motor via gears or belts, or may be mounted directly on the motor spindle or shaft. The controller comprises a processor or microprocessor programmed to control the various functions of the device, including rotation of the wheel or carousel, the timing of rotation or alerts, and authorizing access to the medication. The controller can be programmed directly through an interface on the device, through a port (e.g., USB), or wirelessly (e.g., Bluetooth). A wireless chip or communication device may be present in the device.

A GPS or other location-determining device also may be provided, where the device may be used only within a certain geographic region or area.

When only a set number of filled chambers remain, the device may provide an alert to the user on the display that a refill may be needed. In several embodiments, once a full cycle of access periods had been completed (based on the number of chambers, for example), the device shuts down and does not allow access to any chambers or medications that may have been bypassed or otherwise not removed.

The medication is not stored in bulk, and there are no counting mechanisms or mechanisms to convey or move medication from a storage area to an access area. Instead, each dose is stored in its own chamber, and the chamber is moved to the access area or point when access is indicated. No communication with an outsider server or device is needed, which prevents hacking of the communications or computer programming.

The dispenser can be reusable or single-use (i.e., disposable). In one embodiment, a patient obtains the dispenser pre-loaded from a pharmacist, who sets the timing mechanism and PIN (or provides the PIN to the patient for that particular device) with a master code. The manufacturer can load the appropriate amount of medication in each compartment and ship the dispenser pre-loaded to the physician or pharmacist. In an alternative embodiment, the physician or pharmacist can load the dispenser directly in the clinic or pharmacy. In one embodiment, the physician or pharmacist loads the dispenser by using a limited or master code that causes the chambers to rotate sequentially under the access point for insertion of the medication. In yet a further embodiment, a pre-manufactured disc with medications implanted in the disc (the medications may or may not be covered or secured with plastic or foil) is provided and inserted into the dispenser. A master code may be used to reset the device and establish a new user access code (i.e., if the user forgot their access code).

In one exemplary embodiment, the device comprises 32 chambers, with 30 chambers filled with medication. Each chamber can contain up to two pills, each pill being up to approximately 15 mm (length)×7 mm (width)×5 mm (height). Alternatively, pills can be up to approximately 12 mm in diameter. Keypad buttons are 10 mm in diameter or width, and 11.25 mm apart. The access slot is located at the 2 o'clock or 10 o'clock position on the perimeter, the access period is 1 hour, and the dosing interval is 4 hours.

In order to provide a context for the various computer-related aspects of the invention, the following discussion provides a brief, general description of a suitable computing environment in which the various aspects of the present invention may be implemented. A computing system environment is one example of a suitable computing environment, but is not intended to suggest any limitation as to the scope of use or functionality of the invention. A computing environment may contain any one or combination of components discussed below, and may contain additional components, or some of the illustrated components may be absent. Various embodiments of the invention are operational with numerous general purpose or special purpose computing systems, environments or configurations. Examples of computing systems, environments, or configurations that may be suitable for use with various embodiments of the invention include, but are not limited to, personal computers, laptop computers, computer servers, computer notebooks, hand-held devices, microprocessor-based systems, multiprocessor systems, TV set-top boxes and devices, programmable consumer electronics, cell phones, personal digital assistants (PDAs), tablets, smart phones, touch screen devices, smart TV, internet enabled appliances, internet enabled security systems, internet enabled gaming systems, internet enabled watches; internet enabled cars (or transportation), network PCs, minicomputers, mainframe computers, embedded systems, virtual systems, distributed computing environments, streaming environments, volatile environments, and the like.

Embodiments of the invention may be implemented in the form of computer-executable instructions, such as program code or program modules, being executed by a computer, virtual computer, or computing device. Program code or modules may include programs, objects, components, data elements and structures, routines, subroutines, functions and the like. These are used to perform or implement particular tasks or functions. Embodiments of the invention also may be implemented in distributed computing environments. In such environments, tasks are performed by remote processing devices linked via a communications network or other data transmission medium, and data and program code or modules may be located in both local and remote computer storage media including memory storage devices such as, but not limited to, hard drives, solid state drives (SSD), flash drives, USB drives, optical drives, and internet-based storage (e.g., "cloud" storage).

In one embodiment, a computer system comprises multiple client devices in communication with one or more server devices through or over a network, although in some cases no server device is used. In various embodiments, the network may comprise the Internet, an intranet, Wide Area Network (WAN), or Local Area Network (LAN). It should be noted that many of the methods of the present invention are operable within a single computing device.

A client device may be any type of processor-based platform that is connected to a network and that interacts with one or more application programs. The client devices each comprise a computer-readable medium in the form of volatile and/or nonvolatile memory such as read only memory (ROM) and random access memory (RAM) in communication with a processor. The processor executes computer-executable program instructions stored in memory. Examples of such processors include, but are not limited to, microprocessors, ASICs, and the like.

Client devices may further comprise computer-readable media in communication with the processor, said media storing program code, modules and instructions that, when executed by the processor, cause the processor to execute the program and perform the steps described herein. Computer readable media can be any available media that can be accessed by computer or computing device and includes both volatile and nonvolatile media, and removable and non-removable media. Computer-readable media may further comprise computer storage media and communication media. Computer storage media comprises media for storage of information, such as computer readable instructions, data, data structures, or program code or modules. Examples of computer-readable media include, but are not limited to, any electronic, optical, magnetic, or other storage or transmission device, a floppy disk, hard disk drive, CD-ROM, DVD, magnetic disk, memory chip, ROM, RAM, EEPROM, flash memory or other memory technology, an ASIC, a configured processor, CDROM, DVD or other optical disk storage, magnetic cassettes, magnetic tape, magnetic disk storage or other magnetic storage devices, or any other medium from which a computer processor can read instructions or that can store desired information. Communication media comprises media that may transmit or carry instructions to a computer, including, but not limited to, a router, private or public network, wired network, direct wired connection, wireless network, other wireless media (such as acoustic, RF, infrared, or the like) or other transmission device or channel. This may include computer readable instructions, data structures, program modules or other data in a modulated data signal such as a carrier wave or other transport mechanism. Said transmission may be wired, wireless, or both. Combinations of any of the above should also be included within the scope of computer readable media. The instructions may comprise code from any computer-programming language, including, for example, C, C++, C#, Visual Basic, Java, and the like.

Components of a general purpose client or computing device may further include a system bus that connects various system components, including the memory and processor. A system bus may be any of several types of bus structures, including, but not limited to, a memory bus or memory controller, a peripheral bus, and a local bus using any of a variety of bus architectures. Such architectures include, but are not limited to, Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computing and client devices also may include a basic input/output system (BIOS), which contains the basic routines that help to transfer information between elements within a computer, such as during start-up. BIOS typically is stored in ROM. In contrast, RAM typically contains data or program code or modules that are accessible to or presently being operated on by processor, such as, but not limited to, the operating system, application program, and data.

Client devices also may comprise a variety of other internal or external components, such as a monitor or display, a keyboard, a mouse, a trackball, a pointing device, touch pad, microphone, joystick, satellite dish, scanner, a disk drive, a CD-ROM or DVD drive, or other input or output devices. These and other devices are typically connected to the processor through a user input interface coupled to the system bus, but may be connected by other interface and bus structures, such as a parallel port, serial port, game port or a universal serial bus (USB). A monitor or other type of display device is typically connected to the system bus via a video interface. In addition to the monitor, client devices may also include other peripheral output devices such as speakers and printer, which may be connected through an output peripheral interface.

Client devices may operate on any operating system capable of supporting an application of the type disclosed herein. Client devices also may support a browser or browser-enabled application. Examples of client devices include, but are not limited to, personal computers, laptop computers, personal digital assistants, computer notebooks, hand-held devices, cellular phones, mobile phones, smart phones, pagers, digital tablets, Internet appliances, and other processor-based devices. Users may communicate with each other, and with other systems, networks, and devices, over the network through the respective client devices.

Thus, it should be understood that the embodiments and examples described herein have been chosen and described in order to best illustrate the principles of the invention and its practical applications to thereby enable one of ordinary skill in the art to best utilize the invention in various embodiments and with various modifications as are suited for particular uses contemplated. Even though specific embodiments of this invention have been described, they are not to be taken as exhaustive. There are several variations that will be apparent to those skilled in the art.

What is claimed is:

1. An improved medication dispensing device, comprising:
    a main body comprising an access slot;
    a rotary mechanism contained within said main body, said rotary mechanism comprising a wheel or carousel with an outer perimeter, with a plurality of chambers disposed along said outer perimeter, each of said plurality of chambers with an opening facing said outer perimeter, and a motor mechanically connected to said wheel or carousel, wherein the motor is configured to cause the wheel or carousel to rotate within the main body, thereby causing one of said plurality of chamber openings to rotate to an access position where items in said chamber can exit through an interior passage or conduit connected to said access slot, wherein said interior passage or conduit comprises at least two bends in opposite directions;
    a timer configured to determine specific time periods during which said one of said plurality of chamber openings may be rotated to the access position upon entry and verification of an authorization code input; and
    means to accept said authorization code input.

2. The device of claim 1, wherein said authorization code input means comprises a key pad.

3. The device of claim 1, wherein said authorization code input means comprises a touch display screen.

4. The device of claim 1, wherein said authorization code input means comprises a set of 3 or 4 buttons.

5. The device of claim 1, further comprising an internal power source connected to said motor.

6. The device of claim 4, wherein the internal power source is one or more batteries.

7. The device of claim 1, further comprising a controller with a processor or microprocessor programmed to control rotation of the wheel.

8. The device of claim 1, wherein said access slot remains open.

9. The device of claim 1, wherein said access slot is located on a top of the device.

10. The device of claim 1, wherein said access slot is located on a bottom of the device.

11. The device of claim 1, wherein said access slot is located on a side of the device.

12. The device of claim 1, further comprising a plurality of medications or medicaments disposed in said plurality of chambers.

13. The device of claim 12, wherein each chamber contains an identical dose or amount of medication or medicament.

14. The device of claim 12, wherein the wheel or carousel is interchangeable.

15. The device of claim 14, wherein changing the wheel or carousel requires entry of a second verified authorization code different from the first verified authorized code.

16. The device of claim 7, wherein programming the controller requires entry of a second verified authorization code different from the first verified authorized code.

17. The device of claim 1, wherein said access slot is closable and lockable.

18. The device of claim 1, said interior passage or conduit with a first end at the access position and a second end at the access slot.

19. The device of claim 18, wherein the interior passage or conduit is angled.

20. The device of claim 1, wherein at least one of said bends in the interior passage or conduct bends at an angle between approximately 45 degrees and 90 degrees, and any chamber in access position cannot be accessed directly by a user from outside the main body.

* * * * *